(12) United States Patent
Bart et al.

(10) Patent No.: US 7,087,214 B2
(45) Date of Patent: Aug. 8, 2006

(54) WATER-SOLUBLE PORPHYRIN PLATINUM COMPOUNDS WITH HIGH TUMOR SELECTIVITY AND THEIR USE FOR THE TREATMENT OF BENIGN AND MALIGNANT TUMOR DISEASES

(75) Inventors: Karl Christian Bart, Mühldorf.a Inn (DE); Guenther Bernhardt, Schierling (DE); Henri Brunner, Lappersdorf (DE); Christian Lottner, Neunburg (DE)

(73) Assignee: Zentaris GmbH, Frankfurt am Main (DE)

( * ) Notice: Subject to any disclaimer, the term of this patent is extended or adjusted under 35 U.S.C. 154(b) by 309 days.

(21) Appl. No.: 10/353,788

(22) Filed: Jan. 27, 2003

(65) Prior Publication Data

US 2004/0023942 A1 Feb. 5, 2004

Related U.S. Application Data

(60) Provisional application No. 60/353,585, filed on Feb. 1, 2002.

(51) Int. Cl.
*A61B 5/055* (2006.01)
*A61B 10/00* (2006.01)
*C07B 47/00* (2006.01)
*C07B 5/10* (2006.01)
*A61K 31/555* (2006.01)

(52) U.S. Cl. .................. 424/9.61; 424/9.362; 514/185; 514/410; 534/15; 540/145

(58) Field of Classification Search ................ 540/145; 534/15; 514/185, 410; 424/9.1, 9.362, 9.61
See application file for complete search history.

(56) References Cited

U.S. PATENT DOCUMENTS 4,704,464 A 11/1987 Brunner et al.
4,849,207 A * 7/1989 Sakata et al. ............... 424/1.65

FOREIGN PATENT DOCUMENTS

| EP | 0 193 083 A1 | 9/1986 | |
|---|---|---|---|
| JP | 61083185 A2 * | 4/1986 | ................ 540/145 |
| WO | WO 99/43317 | 9/1999 | |

OTHER PUBLICATIONS

Brunner et al. (Chem. Ber. 1995, (128) 173-181).*
Lindsay et al. (Anal. Chem. 1992 (64) 2804-2814).*
Lemke (REview of Organic Functional Groups, Third Edition, Lea & Febiger, 1995).*
Brunner et al. Platin(II)-Komplexe mit Porphyrinliganden: Synthese und Synergism bei der Photodynamischen Tumortherapie. Chem. Ber. 1995, 128 pp. 173-181.*
Sheldon, Roger. Metalloporphyrins in Catalytic Oxidations. Marcel Dekker. 1994. pp. 218-221.*
Katzung et al. Basic & Clinical Pharmacology. Seventh Edition. Appleton & Lang. 1998. pp. 881-884.*
Henri Brunner and Herbert Obermeier, Platin(II)-Komplexe mit Porphyrinliganden- Additive cytotoxische und photodynamische Wirkung, Angew. Chem 1994, 106, Nr. 21, pp. 2305-2306, XP-002245479.
Henri Brunner, Herbert Obermeier and Rolf-Markus Szeimies, Platin(II)-Komplexe mit Porphyrinliganden: Synthese und Synergismen bei der photodynamischen Tumortherapie, Chem. Ber. 1995, 128, 173-181, XP002245478.
Henri Brunner, Friedrich Maiterth and Barbara Treittinger, Synthese and Antitumoraktivitat neuer Porphyrin-Platin(II)-Komplexe mit an den Porphyrin-Seitenketten gebundenem cytostatischen Platin-Rest, Chem. Ber. 1994, 127, 2141-2149, xp-002108805.
H. Brunner,K-M. Schellerer, B. Treittinger, Synthesis and in vitro testing of hematoporphyrin type ligands in platinum (II) complexes as potent cytostatic and phototoxic antitumor agents, Inorganica Chimica Acta 264 (1997) 67-79, XP-002245477.
T.W. Graham Solomons, Fundamentals of Organic Chemistry, Second Edition, John Wiley & Sons, Inc., 1986, pp. 138-176.
Richard J. Lewis, Sr., Hawley's Condensed Chemical Dictionary, Fourteenth Edition, John Wiley & Sons, Inc., 2001, p. 97.

* cited by examiner

*Primary Examiner*—James O. Wilson
*Assistant Examiner*—Matthew L. Fedowitz
(74) *Attorney, Agent, or Firm*—Goodwin Procter LLP

(57) ABSTRACT

The invention relates to novel, water-soluble porphyrin platinum compounds of the tetraarylporphyrin platinum derivatives type or of the hematoporphyrin platinum derivatives type with high tumor selectivity and their use for the treatment of benign and malignant tumor diseases. In particular, the compounds are suitable for photodynamic antitumor therapy.

22 Claims, 2 Drawing Sheets

WATER-SOLUBLE PORPHYRIN PLATINUM COMPOUNDS WITH HIGH TUMOR SELECTIVITY AND THEIR USE FOR THE TREATMENT OF BENIGN AND MALIGNANT TUMOR DISEASES

This is a nonprovisional application based on provisional application Ser. No. 60/353,585, filed on Feb. 1, 2002.

INTRODUCTION

The invention relates to novel, water-soluble porphyrin platinum compounds with high tumor selectivity and their use for the treatment of benign and malignant tumor diseases. In particular, the inventive compounds are suitable for photodynamic anti-tumor therapy in man and mammals.

PRIOR ART

Platinum(II) complexes with porphyrin ligands and their application as potent cytostatic and phototoxic antitumor agents have already been described in the following publications.

W. M. Sharman, C. M. Allen and J. E. van Lier, DDT 4, (11) 507–517 (1999). Photodynamic therapeutics: basic principles and clinical applications T. Okunaka and H. Kato, Rev. Contemp. Pharmacother., 10, 59–68 (1999). Potential Applications of Photodynamic Therapy.

H. Brunner, H. Obermeier and R.-M. Szeimies, Chem. Ber., 1995, 128, 173–181. Platinum(II) complexes with porphyrin ligands: synthesis and synergism during photodynamic therapy.

H. Brunner, K.-H. Schellerer and B. Treittinger, Inorg. Chim. Acta 1997, 264, 67–69. Synthesis and in vitro testing of hematoporphyrin type ligands in platinum(II) complexes as potent cytostatic and phototoxic antitumor agents.

DESCRIPTION OF THE INVENTION

Figure 1:
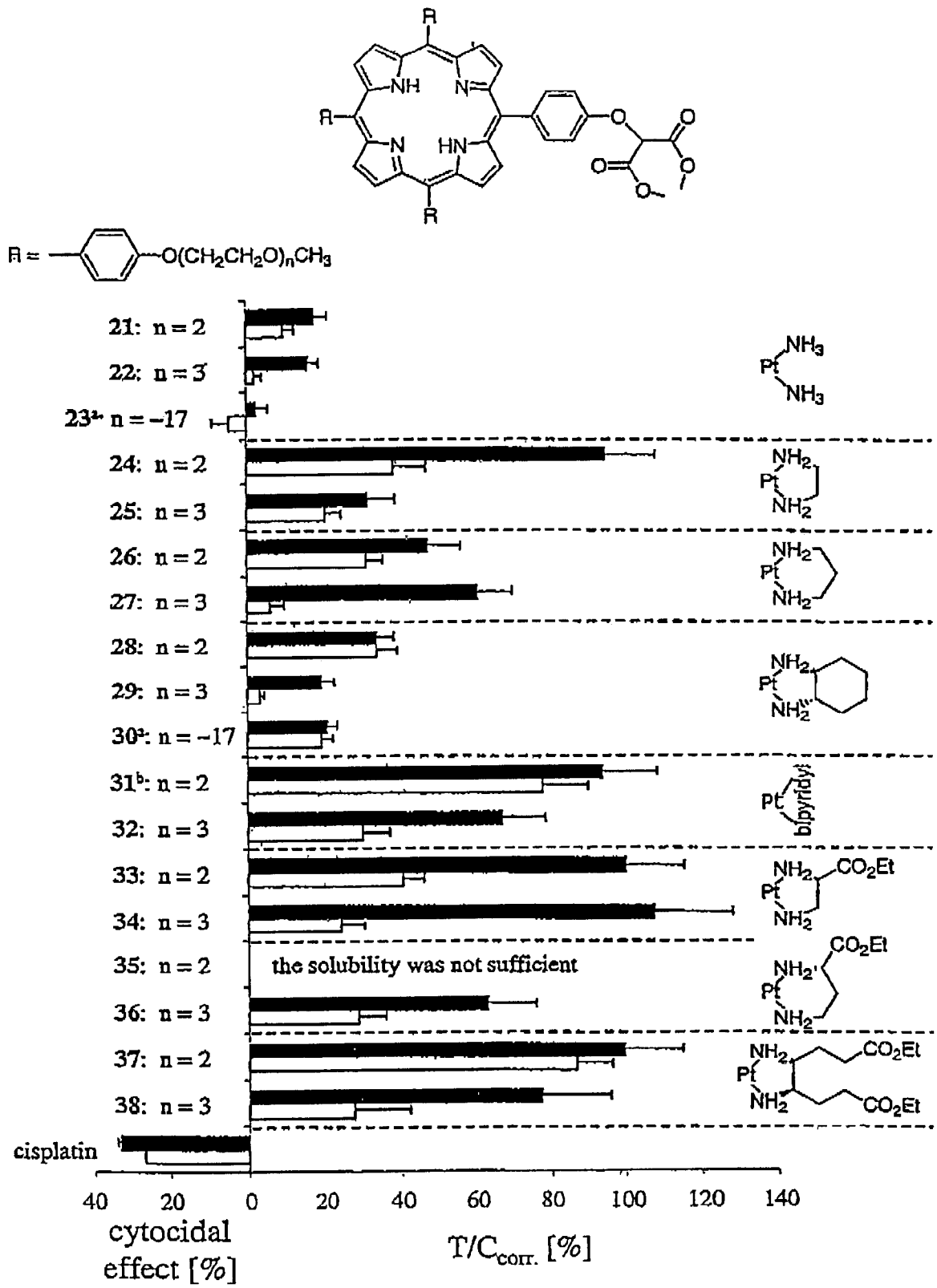

In the invention, novel porphyrin platinum derivatives are described, which have cytotoxic properties. Surprisingly, the compounds have good water solubility and a high selectivity. The compounds can be used for the treatment of cancer and, in particular, for the photodynamic treatment of tumors.

The general formulas of the claimed compounds of the tetraarylporphyrin platinum derivatives type are:

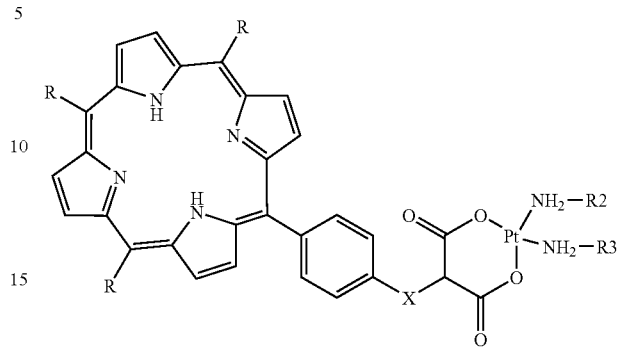

Formula I

X: O, S, NH, N-Alkyl
R2/R3: H, Alkyl, Aryl, Aralkyl, Hetaryl, Hetarylalkyl, Cylcoalkyl
R4: H, Alkyl, Aryl, Aralkyl, Hetaryl, Hetarylalkyl, Cycloalkyl
R5: H, Alkyl, O-Alkyl, S-Alkyl, Halogen, Nitro, Cyano, Amino, subst. Amino
R6: H, Alkyl, O-Alkyl, S-Alkyl, Halogen, Nitro, Cyano, Amino, subst. Amino Formula II X: O, S, NH, N-Alkyl
R1/R2/R3/R4: H, Alkyl, Aryl, Aralkyl, Hetaryl, Hetarylalkyl, Cylcoalkyl
oder, $R_2-Z-R_3$, mit Z: $(CH_2)_n$, n = 0–6
R1/R4: H, $-(CH_2)_n-$, $-COOR8$, n = 0–6
R5: H, Alkyl, Aryl, Aralkyl, Hetaryl, Hetarylalkyl, Cycloalkyl
R6: H, Alkyl, O—Alkyl, S—Alkyl, Halogen, Nitro, Cyano, Amino, subst.Amino
R7: H, Alkyl, O—Alkyl, S—Alkyl, Halogen, Nitro, Cyano, Amino, subst. Amino
R8: H, Alkyl The general formulas of the claimed compounds of the hematoporphyrin platinum derivatives type are:

Formula III

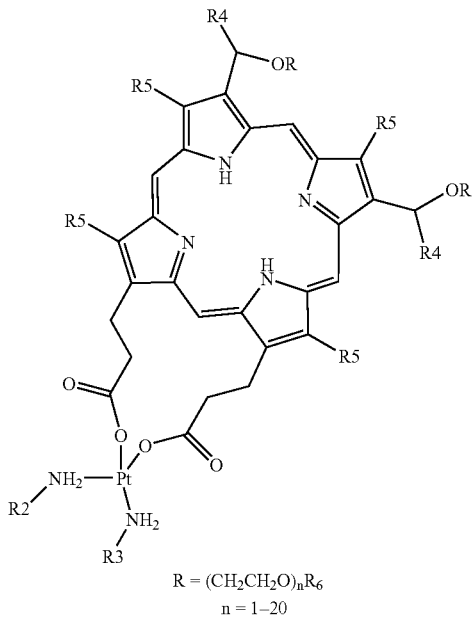

R = (CH$_2$CH$_2$O)$_n$R$_6$
n = 1–20

R2/R3: H, Alkyl, Aryl, Aralkyl, Hetaryl, Hetarylalkyl, Cylcoalkyl
R4: H, Alkyl, Cycloalkyl
R5: H, Alkyl, Cycloalkyl
R6: H, Alkyl, Aryl, Aralkyl, Hetaryl, Hetarylalkyl, Cycloalkyl Formula IV

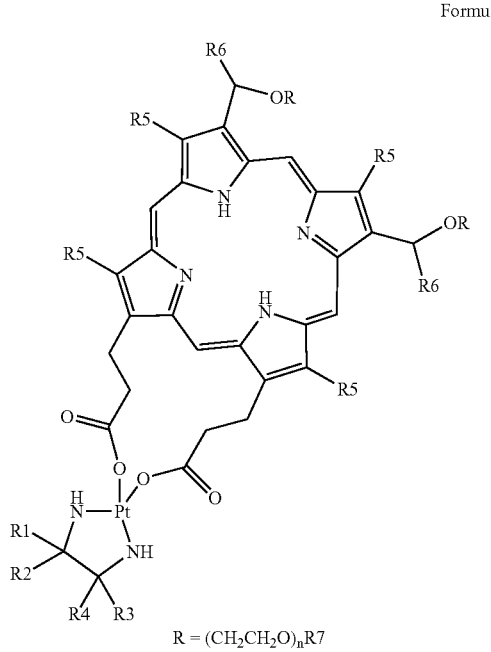

R = (CH$_2$CH$_2$O)$_n$R$_7$
n = 1–20

R1/R2/R3/R4: H, Alkyl, Aryl, Aralkyl, Hetaryl, Hetarylalkyl, Cylcoalkyl
oder R2—Z—R4, mit Z: (CH$_2$)$_n$, n = 0–6
oder R1/R3: H, —(CH$_2$)$_n$, —COOR6, n = 0–6
R4/R5: H, Alkyl, Aryl, Aralkyl, Hetaryl, Hetarylalkyl, Cycloalkyl
R6: H, Alkyl, Aryl, Aralkyl, Hetaryl, Hetarylalkyl, Cycloalkyl
R7: H, Alkyl, Aryl, Aralkyl, Hetaryl, Hetarylalkyl, Cycloalkyl If the inventive compounds have at least one center of asymmetry, they can be in the form of their racemates, their pure enantiomers and/or their diastereoisomers or in the form of mixtures of these enantiomers or diastereoisomers.

The inventive compounds exhibit cytotoxic activity in selected tumor cell lines. The antitumor activity is intensified by irradiating with electromagnetic radiation having a wavelength of 600 to 730 nm. The invention accordingly relates to the chemical combination of the cytotoxic principle of the platinum compounds of the cis platinum type with a photodynamically active molecule of the porphyrin derivative type, in such a manner, that compounds of good water solubility and high selectivity are obtained.

The inventive compounds can be administered intraaterially, intracerebrally, intramuscularly, intraperitoneally, intrathecally, intravenously, orally, parenterally, intranasally, rectally, subcutaneously and/or topically in the form of tablets, film-coated tablets, capsules, coated tablets, powders, granulates, drops, syrups, ointments, powders for inhalation, infusion solutions, drinking solutions or in some other suitable form.

The medicaments comprise one or more compounds in addition to customary physiologically tolerable carriers and/or diluents or auxiliaries.

The process for the production of the medicament is characerized in that one or more compounds are processed to give pharmaceutical preparations or brought into a therapeutically administrable form using customary pharmaceutical carriers and/or diluents or other auxiliaries.

The synthesis of the inventive compounds is described.

Tetraarylporphyrin Platinum Derivatives

Synthesis of the substituted benzaldehydes. For the reaction with 4-hydroxy-benzaldehyde the respective oligo- and polyethyleneglycol monomethylethers had to be activated at their alcohol terminus with tosyl chloride according to a literature procedure. The etherification was performed by refluxing the tosylated alcohols and 4-hydroxybenzaldehyde together with K$_2$CO$_3$ in DMF. The substituted benzaldehydes were separated by filtration and purified by column chromatography.

For platinum coordination to the tetraarylporphyrins to be synthesized it is necessary to introduce two adjacent carboxylic acid groups in one of the substituted benzaldehydes. Therefore, 4-hydroxybenzaldehyde was etherified with diethyl bromomalonate under alkaline conditions. The diethyl 2-(4-formylphenoxy)malonate was used together with the substituted benzaldehydes for the synthesis of asymmetric tetraarylporphyrins.

Synthesis of the porphyrin ligands. The synthesis of the asymmetric tetraarylporphyrins was performed using the Lindsey method. Pyrrol and the respective benzaldehydes were reacted under Lewis acid catalysis to porphyrinogens, which were oxidized with p-chloranil to the corresponding porphyrins. The tetraarylporphyrin esters were purified by several column chromatographies. The carboxylic acids, which were required for coordination to the platinum(II) fragments, were prepared by hydrolysis of the esters with a mixture of CHCl$_3$ and 20% methanolic KOH solution or pure 20% methanolic KOH solution only.

Synthesis of the platinum fragments. 1,2-Diaminoethane, 1,3-diaminopropane, trans-1,2-diaminocyclohexane and 2,2'-bipyridine were commercially available and used as ligands to prepare the corresponding dichloroplatinum(II) complexes according to literature procedures. Ethyl DL-2,3-diaminopropionate dihydrochloride, ethyl L-2,4-diaminobutanoate dihydrochloride and diethyl meso-4,5-diaminosuberate dihydrochloride were synthesized according to literature procedures and used as ligands for the preparation of the corresponding diiodoplatinum(II) complexes.

Synthesis of the platinum complexes. For the reaction with the porphyrincarboxylic acids cisplatin had to be activated by conversion into diammine(diaqua)platinum(II) hydroxide. It was reacted with an equimolar amount of the porphyrin ligand in a mixture of CHCl$_3$, ethanol and water or, in the case of the water-soluble ligand, in pure water. The resulting diammine(malonato)platinum(II) complexes precipitated. To the reaction mixture of the water-soluble complex CH$_2$Cl$_2$ was added to remove neutral impurities. The aqueous hphase was evaporated to obtain the product.

The diamine(dichloro)platinum(II) fragments were activated by conversion into diamine(dihydroxy)platinum(II) species, which were reacted with an equimolar amount of the respective porphyrin malonic acid in a mixture of CH$_2$Cl$_2$, ethanol and water or, in the case of the water-soluble ligand, in pure water. The complexes precipitated. To the water-soluble complex CH$_2$Cl$_2$ was added to remove neutral impurities, before the aqueous phase was evaporated to obtain the product.

For the reaction with the porphyrinmalonic acids it was necessary to activate the diamine(diiodo)platinum(II) complexes by conversion into diamine(dinitrato) platinum(II) species, which are water-soluble. In this form they were reacted with an equimolar amount of the porphyrin ligands, in a mixture of CH$_2$Cl$_2$, ethanol and water. The water-insoluble complexes precipitated after concentrating the solutions.

Hematoporphyrin Platinum Derivatives Type

Synthesis of the porphyrin ligands and the platinum precursors. Hemin was transferred to protoporphyrin dimethylester, from which all the subsequent reactions started. First, protoporphyrin dimethylester was treated with 30% hydrobromic acid in acetic acid to give the labile Markownikoff adduct of HBr to the two vinyl double bonds, which was reacted with different types of alcohols to replace bromide by the corresponding alkoxides. As alcohols we chose hydrophilic oligo- and polyethyleneglycol monomethylethers. During the etherification the HBr formed catalyzed the transesterification of the methylesters into the esters of the corresponding alcohols. The etherified hematoporphyrin esters were purified by column chromatography. The carboxylic acids, which were required for coordination to the platinum(II) moieties, were prepared by hydrolysis of the esters with 20% methanolic KOH solution.

1,2-Diaminoethane, 1,3-diaminopropane, trans-1–2-diaminocyclohexane and 2,2'-bi-pyridine were commercially available and used as ligands to prepare the corresponding dichloroplatinum(II) complexes according to literature procedures. Ethyl DL-2,3-diaminopropionate dihydrochloride, ethyl L-2,4-diaminobutanoate dihydrochloride and diethyl meso-4,5-diaminosuberate dihydrochloride were synthesized according to literature procedures and used as ligands for the preparation of the corresponding diiodoplatinum(II) complexes.

Synthesis of the platinum complexes. Reaction of the porphyrin carboxylic acids with cisplatin did not result in the desired complexes. Therefore, cisplatin had to be activated by conversion into diammine(diaqua)platinum(II) hydroxide, which was reacted with an equimolar amount of the porphyrin ligand in a mixture of ethanol and water or, in the case of the water-soluble ligands, in pure water. The resulting diammine(dicarboxylato)platinum(II) complexes precipitated. To the reaction mixtures of the water-soluble complexes CH$_2$Cl$_2$ was added to remove neutral impurities before the aqueous phase was evaporated to obtain the products.

The diamine(dichloro)platinum(II) precursors were activated by conversion into diamine(dihydroxy)platinum(II) species, which were reacted with an equimolar amount of the respective porphyrin carboxylic acid in a mixture of ethanol and water or, in the case of the water-soluble ligands, in pure water. The complexes precipitated. To the water-soluble complex CH$_2$Cl$_2$ was added to remove neutral impurities and the aqueous phase was evaporated to obtain the product.

For the reaction with the porphyrincarboxylic acids it is necessary to activate the diamine(diiodo)platinum(II) complexes by conversion into diamine(dinitrato) platinum(II) species, which are water-soluble. In this form they were reacted with an equimolar amount of the porphyrin ligand in a mixture of ethanol and water or, in the case of the water-soluble ligand, in pure water. The water-insoluble complexes precipitated after concentrating the solution. The water-soluble complexes were isolated by chromatography on silica.

Exemplary Embodiments

The following examples are intended to explain the invention in more detail. The inventive compounds are tetraarylporphyrin platinum derivatives, covered by way of example by examples 1 and 2, and hematoporphyrin platinum derivatives, covered by way of example by examples 3, 4 and 5.

EXAMPLES

Example 1

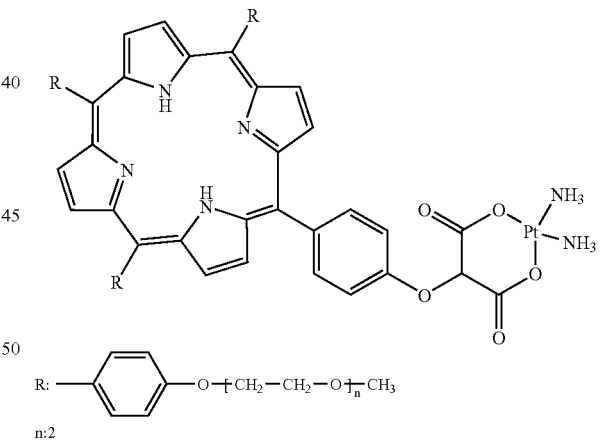

Diammine[2-(4-{10,15,20-tris[4-(1,4,7-trioxaoctyl)phenyl]porphyrin-5-yl}phenoxy)malonato]platinum(II) (No. 21 in FIG. 1)

The compound 2-(4-{10,15,20-Tris[4-(1,4,7-trioxaoctyl) phenyl]porphyrin-5-yl}phenoxy)malonic acid (109 mg, 0.100 mmol) was dissolved in 10 ml of CHCl$_3$ and 20 ml of EtOH, combined with 0.100 mmol of the aqueous diammine (diaqua)platinum(II) hydroxide solution and stirred for 20 h. Yield: 81.0 mg (54.2 μmol, 54%) purple powder, mp 213–214° C.

Anal. (C$_{62}$H$_{66}$N$_6$O$_{14}$Pt.10H$_2$O, 1494,5) C: calcd. 49,83; found. 49,19. H, N: calcd. 5,62; found 6.09.

Example 2

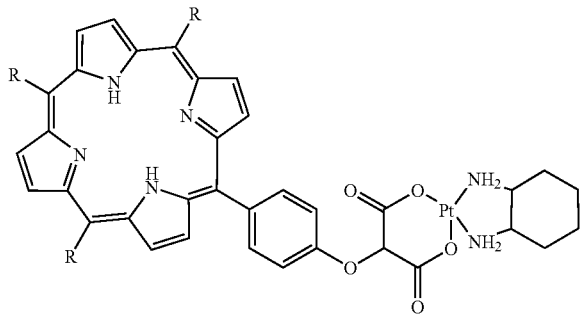

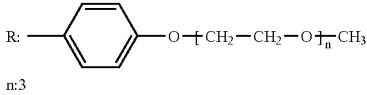
n:3

(+)-trans-1,2-Diaminocyclohexane[2-(4-{10,15,20-tris[4-(1,4,7,10-tetraoxaundecyl)phenyl]porphyrin-5-yl}phenoxy)malonato]platinum(II) (No. 29 in FIG. 1).

122 mg (0.100 mmol) Of the compound 2-(4-{10,15,20-Tris[4-(1,4,7,10-tetraoxaundecyl)phenyl]porphyrin-5-yl}phenoxy)malonic acid in 10 ml of $CH_2Cl_2$ and 20 ml of EtOH were reacted with 0.100 mmol of activated (+)-trans-1,2-diaminocyclohexane(dichloro)platinum(II). Yield: 113 mg (73.9 μmol, 74%) purple solid, mp 208° C. Anal. ($C_{74}H_{86}N_6O_{17}Pt$, 1526.6) C, H, N.

Example 3

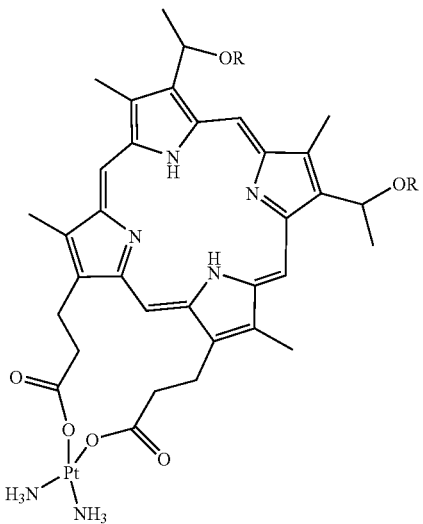

R = $(CH_2CH_2O)_nCH_3$
n = 2

Figure 2:
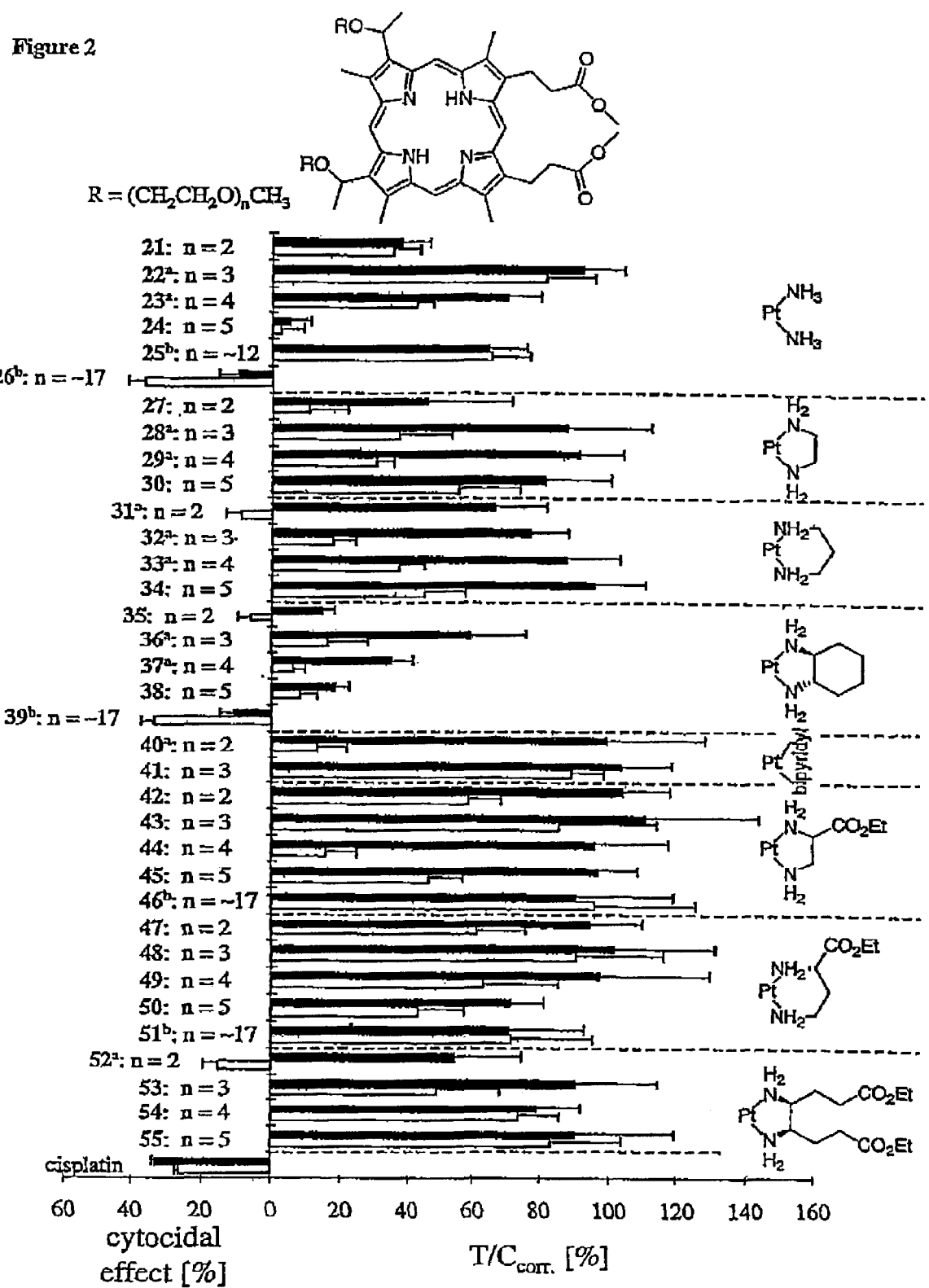
FIG. 2 shows comparative data of the cytotoxic effect of additional compounds on human bladder tumor cells in the dark and under irradiation with light at a wavelength of 600–730 nm.

Diammine{7,12-bis[1-(1,4,7-trioxaoctyl)ethyl]-3,8,13,17-tetramethylporphyrin-2,18-dipropionato}platinum(II) (No. 21 in FIG. 2).

The compound 7,12-Bis[1-(1,4,7-trioxaoctyl)ethyl]-3,8,13,17-tetramethylporphyrin-2,18-dipropionic acid (80.3 mg, 0.100 mmol) was dissolved in 6 ml EtOH, combined with 0.100 mmol of the aqueous diammine(diaqua)platinum(II) hydroxide solution and stirred for 20 h. Yield: 23.0 mg (22.3 μmol, 22%) dark brown powder, mp>250° C. Anal. ($C_{44}H_{62}N_6O_{10}Pt$, 1030.1). C: calcd. 51.30; found. 50.75. H: calcd. 6.07; found. 5.49. N

Example 4

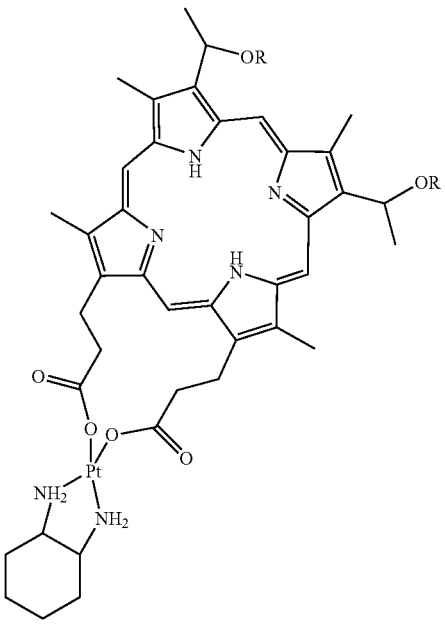

R = $(CH_2CH_2O)_nCH_3$
n = 5

(+)-trans-1,2-Diaminocyclohexane{7,12-bis[1-(1,4,7,10,13,16-hexaoxaheptadecyl)ethyl]-3,8,13,17-tetramethylporphyrin-2,18-dipropionato}platinum(II) (No. 38 in FIG. 2).

The compound 7,12-Bis[1,4,7,10,13,16-hexaoxaheptadecyl)ethyl]-3,8,13,17-tetramethylporphyrin-2,18-dipropionic acid (107 mg, 0.100 mmol) in 10 ml of EtOH were reated with 0.100 mmol of activated (+)-trans-1,2-Diaminocyclohexane(dichloro)platinum(II).

Yield: 25.5 mg (17.2 μmol, 17%) reddish brown powder; mp 245° C. Anal. ($C_{62}H_{94}N_6O_{16}Pt.6 H_2O$, 1482,6). C: calcd. 50.23; found. 49.02. H: calcd. 7.21; found. 6.33. N: calcd. 5,67; found. 6.41.

Example 5

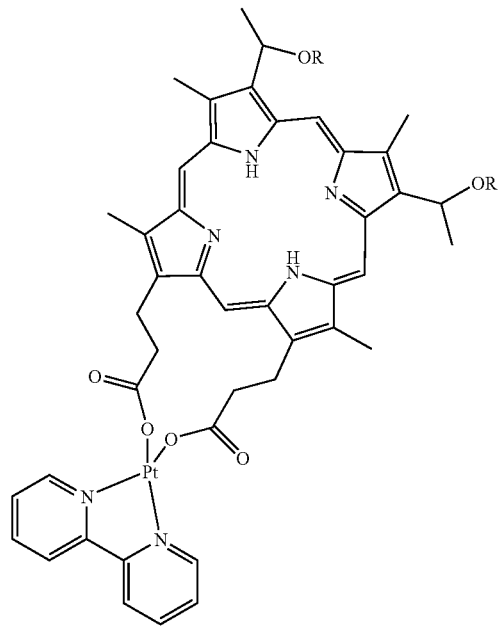

R = (CH$_2$CH$_2$O)$_n$CH$_3$
n = 2

2,2'-Bipyridyl{7,12-bis[1-(1,4,7-trioxaoctyl)ethyl]-3,8,13,17-tetramethylporphyrin-2,18-dipropionato}platinum(II) (No. 40a in FIG. 2).

42.2 mg (0.100 mmol) of the compound 2,2'-Bipyridyl (dichloro)platinum(II) were suspended in 15 ml of H$_2$O. After 10 min ultrasonic treatment 34.0 mg (0.200 mmol) of AgNO$_3$ were added and the mixture was stirred for 4 h in the dark at room temperature. The precipitated AgCl was filtered off and washed with water. The filtrate containing the activated platinum(II) complex was evaporated. The residue was dissolved in 5 ml of H$_2$O and combined with a solution of 80.3 mg (0.100 mmol) 7,12-Bis[1-(1,4,7-trioxaoctyl)ethyl]-3,8,13,17-tetramethylporphyrin-2,18-dipropionic acid in 10 ml of EtOH. After stirring for 20 h at 50° C. and cooling to room temperature the precipitated solid was filtered, washed with water and EtOH and dried in vacuo.

Yield: 64.0 mg (55.5 μmol, 55%) dark purple powder, mp>250° C. Anal. (C$_{54}$H$_{64}$N$_6$O$_{10}$Pt, 1152.2) C, H, N.

Biological Data.

Data of the cytotoxic effect was obtained, for instance, on the human tumor cell lines TCC-SUP and J82. The effect of the compounds was investigated in the dark and under irradiation with light at a wavelength of 600–730 nm. Selected compounds are clearly more activ cytotoxically under irradiation. There is a synergism between the cytotoxic effect of the platinum component and the photodynamic principle.

Cell Lines and General Procedures.

To determine the antiproliferative activity of the new porphyrin ligands and the corresponding platinum complexes with different amine non-leaving groups two bladder cancer cell lines TCC-SUP and J82 were selected as in vitro models.

To discriminate between the cytotoxic and phototoxic effects all experiments were carried out in duplicate. The cells were seeded into microplates and the test compounds were added after 48 h. One batch of the microplates was kept in the dark until the end of the experiment, whereas the other microplates were irradiated 48 h after addition of the substances for 10 min with a light dose of 24 J·cm$^{-2}$, before the plates were reincubated in the dark.

End-Point Chemosensitivity Assay.

Hematoporphyrin Platinum Derivatives Type.

At a dosage of 1 μM, both the dark- and phototoxicity of the porphyrin-platinum conjugates are influenced by the type of the non-leaving group. The platinum complexes with 2,2'-bipyridyl (40, 41), ethyl DL-2,3-diaminopropionate (42–46), ethyl DL-2,3-diaminobutanoate (47–51), diethyl meso-4,5-diaminosuberate (52–55) ligands were inactive at a concentration of 1 μM, both in the dark and after irradiation. The compounds bearing 1,2-diaminoethane (27–30) and 1,2-diaminopropane (31–34) non-leaving groups were also inactive against TCC-SUP cells. The most interesting porphyrin-platinum conjugates were those with the diammine (21–26) and the (+)-trans-1,2-diaminocyclohexane (35–39) ligands. Within these series of compounds the water-soluble complexes 26 and 39 were most active with T/C$_{corr.}$ of around 30% and 15%, respectively. At 1 μM concentration the reference cisplatin had a T/C$_{corr.}$ value of approximately 2%. At this dosage there was no statistically significant enhancement of the cytotoxicity by irradiation of the bladder cancer cells.

An increase in the concentration of complexes 40–55 to 5 μM resulted in no or only marginal augmentation of the dark toxicity (FIG. 2). For most of these complexes the phototoxicity is not much higher than the cytotoxicity observed without irradiation. However, for 42, 45, 47, 49, 50 and 53 there is a distinct effect and for 40 and 44 a very strong effect on the proliferativation of the TCC-SUP cells upon irradiation is observed (FIG. 2). The highest synergism was found for compound 52 resulting in the lysis of the tumor cells.

Apart from cisplatin, the highest antitumor activities were measured within the series of porphyrin-platinum conjugates bearing diammine (21–26) and (+)-trans-1,2-diaminocyclohexane (35–39) non-leaving groups. The differences between dark and light-induced toxicities were best for the water-soluble porphyrin-platinum complexes 26 and 39 with a side chain length of n≈17 in position 7 and 12 of the porphyrin leaving group. All the ethylenediamine and propylenediamine complexes 27–34 showed a remarkable light-induced toxicity (FIG. 2).

Tetraarylporphyrin Platinum Derivatives Type.

At a dosage of 1 μM and 5 μM, both the dark- and phototoxicity of the tetraarylporphyrin-platinum conjugates 21–38 were highly influenced by the type of the non-leaving group the results agreeing with those of the hematoporphyrin-platinum complexes discussed above. 23, 29 and 30 were the most active tetraarylporphyrin-platinum conjugates with T/C$_{corr.}$ values of around 37%, 57% and 63%, respectively, at 1 μM concentration. This is analogous to the hematoporphyrin-platinum complexes, the most active of which were those with the diammine or the (+)-trans-1,2-diaminocyclohexane non-leaving groups. At 1 μM concentration there was only a slight enhancement of the cytotoxicity of the tetraarylporphyrin-platinum conjugates with the side chain length n=2 and n=3 upon irradiation. On the average the light-induced T/C$_{corr.}$ values were by approximately 20% lower than the dark-only cytotoxicities (data not shown). An increase in the concentration of the complexes to 5 μM enhanced the dark effects and the phototoxicities as shown in FIG. 1. Apart from cisplatin, the highest antitumor activities were measured for the tetraarylporphyrin-platinum conjugates bearing diammine (21–23) and (+)-trans-1,2-diaminocyclohexane (28–30) non-leaving groups. The differences between dark and light-induced toxicities were best for the tetraarylporphyrin-platinum complexes 24, 27, 32–34, 36 and 38 with a side chain length of n=2 or n=3 (FIG. 1).

What is claimed is:

1. A porphyrin platinum derivative of the (a) tetraarylporphyrin platinum derivative type according to formula I

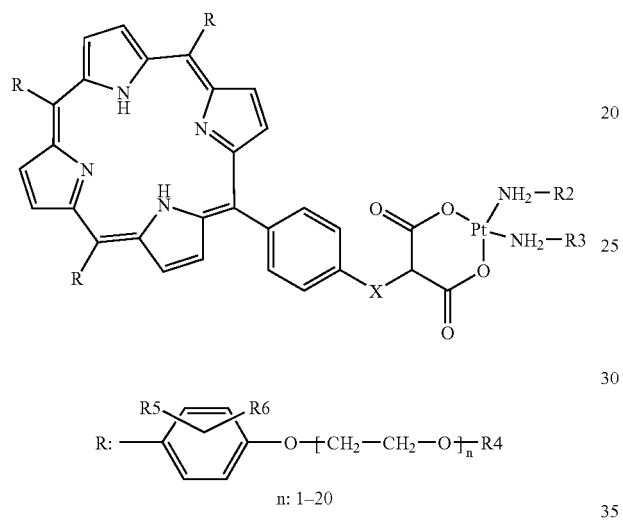

n: 1–20

X: O, S, NH, N-Alkyl
R2 and R3: H, Alkyl, Aryl, Aralkyl, Hetaryl, Hetarylalkyl, Cylcoalkyl
R4: H, Alkyl, Aryl, Aralkyl, Hetaryl, Hetarylalkyl, Cycloalkyl
R5: H, Alkyl, O-Alkyl, S-Alkyl, Halogen, Nitro, Cyano, Amino, subst. Amino
R6: H, Alkyl, O-Alkyl, S-Alkyl, Halogen, Nitro, Cyano, Amino, subst. Amino or according to formula II n: 1–20
X: O, S, NH, N-Alkyl
R1, R2, R3 and R4: H, Alkyl, Aryl, Arylalkyl, Heteroaryl, Heteroarylalkyl, Cycloalkyl
or R2—Z—R3, with Z: $(CH_2)_n$, n = 0–6
R1 and R4: H, —$(CH_2)_n$—COOR8, n = 0–6
R5: H, Alkyl, Aryl, Arylalkyl, Heteroaryl, Heteroarylalkyl, Cycloalkyl
R6: H, Alkyl, O-Alkyl, S-Alkyl, Halogen, Nitro, Cyano, Amino, substituted Amino
R7: H, Alkyl, O-Alkyl, S-Alkyl, Halogen, Nitro, Cyano, Amino, substituted Amino or (b) hematoporphyrin platinum derivative type according to formula IV R= $(CH_2CH_2O)_nR7$
n=1–20

R1, R2, R3 and R4: H, Alkyl, Aryl, Aralkyl, Hetaryl, Hetarylalkyl, Cylcoalkyl
or R2 and R4 together form a ring with a $(CH_2)_n$ chain with n = 1–6,
or R1 and R3: H, —$(CH_2)_n$, —COOR6, n = 0–6
R4 and R5: H, Alkyl, Aryl, Aralkyl, Hetaryl, Hetarylalkyl, Cycloalkyl
R6: H, Alkyl, Aryl, Aralkyl, Hetaryl, Hetarylalkyl, Cycloalkyl
R7: H, Alkyl, Aryl, Aralkyl, Hetaryl, Hetarylalkyl, Cycloalkyl.

2. A compound according to claim 1, being in the form of a racemate, enantiomer or diastereoisomer thereof.

3. A method for photodynamic treatment of a cancer, comprising administering a compound according to claim 1 to a patient in need thereof.

4. A method for photodynamic treatment of a tumor, comprising administering a compound according to claim 1 to a patient in need thereof.

5. The method of claim 4, further comprising irradiating with electromagnetic radiation having a wavelength of 600 to 730 nm.

6. A composition comprising one or more compounds according to claim 1 and a physiologically tolerable carrier, diluent or auxiliary.

7. A method for photodynamic treatment of a cancer, comprising administering a compound according to claim 2 to a patient in need thereof.

8. A method for photodynamic treatment of a tumor, comprising administering a compound according to claim 2 to a patient in need thereof.

9. The method of claim 8, further comprising irradiating with electromagnetic radiation having a wavelength of 600 to 730 nm.

10. A composition comprising one or more compounds according to claim 2 and a physiologically tolerable carrier, diluent or auxiliary.

11. The compound according to claim 1, selected from the group consisting of:
Diammine[2-(4-[10,15,20-tris[4-(1,4,7-trioxaocryl)phenyl]porphyrin-5-yl } phenoxy)malonato]platinum (II);

(±)-trans-1,2-Diaminocyclohexane[2-(4{ 10,15,20-tris[4-(1,4,7,10-tetraoxaundecyl)phenyl]porphyrin-5-yl} phenoxy) malonato[platinum(II)];

(±)-trans-1,2-Diaminocyclohexane{7,12-bis[1-( 1,4,7,10,13,16-hexaoxaheptadecyl) ethyl]-3,8,13,17-tetramethylporphyrin-2,18-dipropionato} platinum(II); and 2,2'-Bipyridyl (7,12-bis[1-(1,4,7-trioxaocryl)ethyl]3,8,13,17-tetramethylporphyrin-2,18-dipropionato } platinum(II).

12. A method for photodynamic treatment of a cancer, comprising administering a compound according to claim 11 to a patient in need thereof.

13. A method for photodynamic treatment of a tumor, comprising administering a compound according to claim 11 to a patient in need thereof.

14. The method of claim 13, further comprising irradiating with electromagnetic radiation having a wavelength of 600 to 730 nm.

15. A composition comprising one or more compounds according to claim 11 and a physiologically tolerable carrier, diluent or auxiliary.

16. A porphyrin platinum derivative of the hematoporphyrin platinum derivative type according to formula III

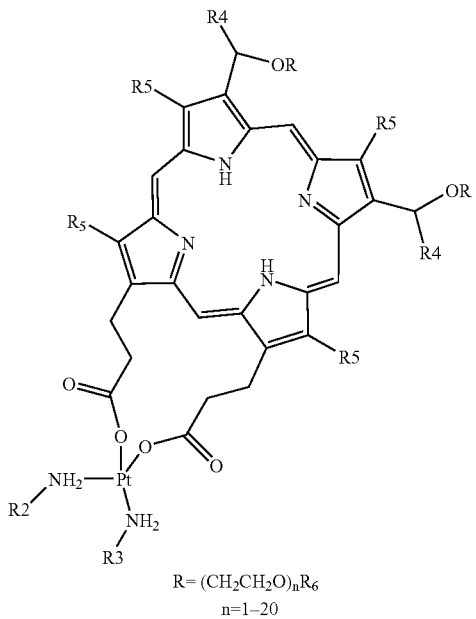

R= $(CH_2CH_2O)_nR_6$
n=1–20

-continued

R2 and R3: H, Alkyl, Aryl, Aralkyl, Hetaryl, Hetarylalkyl, Cylcoalkyl
R4: H, Alkyl, Cycloalkyl
R5: H, Alkyl, Cycloalkyl
R6: H, Alkyl, Aryl, Aralkyl, Hetaryl, Hetarylalkyl, Cycloalkyl.

17. The compound of claim 16, wherein n=1-8.

18. The compound of claim 16, which is diammine{7,12-bis[1-(1,4,7-trioxaoctyl)ethyl]-3,8,13,17-tetramethylporphyrin-2,18-dipropionato } platinum(II).

19. A method for phorodynamic treatment of a cancer, comprising administering a compound according to claim 16 in a patient in need thereof.

20. A method for photodynamic treatment of a tumor, comprising administering a compound according to claim 16 to a patient in need thereof.

21. The method of claim 20, further comprising irradiating with electromagnetic radiation having a wavelength of 600 to 730 nm.

22. A composition comprising one or more compounds according to claim 16 and a physiologically tolerable carrier, diluent or auxiliary.

* * * * *